United States Patent [19]

Dávid et al.

[11] Patent Number: 5,022,972

[45] Date of Patent: Jun. 11, 1991

[54] PROCESS FOR MEASURING AND DETERMINING ZETA-POTENTIAL IN A LAMINARLY FLOWING MEDIUM FOR PRACTICAL PURPOSES

[75] Inventors: Ágoston Dávid; Márai K. Dávid; István Rácz, all of Budapest, Hungary

[73] Assignee: MTA Kutatási Eszközöket Kivitelező Vállata, Budapest, Hungary

[21] Appl. No.: 269,664

[22] PCT Filed: Dec. 5, 1987

[86] PCT No.: PCT/HU87/00048

§ 371 Date: Jun. 20, 1988

§ 102(e) Date: Jun. 20, 1988

[87] PCT Pub. No.: WO88/03265

PCT Pub. Date: May 5, 1988

[51] Int. Cl.$^5$ .................... G01N 27/447; G01N 27/26
[52] U.S. Cl. .............................. 204/183.3; 204/299 R; 204/180.1
[58] Field of Search ............... 204/299 R, 183.3, 1 T, 204/180.1

[56] References Cited

U.S. PATENT DOCUMENTS

| | | | |
|---|---|---|---|
| 3,454,487 | 7/1969 | Riddick | 204/183.3 X |
| 3,708,402 | 1/1973 | Bean | 204/183.3 X |
| 3,723,712 | 3/1973 | Komline Sr. et al. | 204/299 R X |
| 3,764,512 | 10/1973 | Greenwood et al. | 204/183.3 X |
| 4,097,153 | 6/1978 | DeRemigis | 204/180.1 X |
| 4,113,596 | 9/1978 | Treille et al. | 204/299 R X |
| 4,203,817 | 5/1980 | Schütt et al. | 204/249 R X |
| 4,433,290 | 2/1984 | Kawai et al. | 204/183.3 X |
| 4,456,513 | 6/1984 | Kawai et al. | 204/183.3 X |

FOREIGN PATENT DOCUMENTS 210351  6/1984  German Democratic Rep. .................. 204/299 R Primary Examiner—John F. Niebling
Assistant Examiner—John S. Starsiak, Jr.
Attorney, Agent, or Firm—Schweitzer & Cornman

[57] ABSTRACT

The invention relates to a measuring method for determining the zeta-potential ZP of a material suspended in a liquid medium which comprises streaming the suspension in a laminar flow, subjecting the system to the effect of D.C. voltage, and determining the electroporetic velocity from the change of a flow velocity of a selected particle.

3 Claims, 2 Drawing Sheets

PROCESS FOR MEASURING AND DETERMINING ZETA-POTENTIAL IN A LAMINARLY FLOWING MEDIUM FOR PRACTICAL PURPOSES

BACKGROUND AND SUMMARY OF THE INVENTION

The invention relates to a new process for measuring the zeta-potential on the surface of a material suspended in a liquid medium. The measuring is carried out, at simultaneously regulated flow velocity and voltage values, in a visually controlled measuring pipe provided with two electrodes.

According to the experiences of Smoluchowski, M. [Handbuch der Elektrizität und Magnetismus, Ed. L. Grätz, (Barth Verlag, Leipzig 1921) Volume II, page 366] if a material suspended in liquid is subjected to the effect of steady voltage, the particles migrate. Based on the electrophoretic velocity (migration speed) ($v_e = cm.s^{-1}$) and the electric voltage density applied ($E = V.cm^{-1}$, wherein $V$ = voltage in Volts and cm = the distance between the electrodes in cm) the zeta-potential (ZP) characteristic for the material can be determined, while the positive or negative polarity thereof depends on the direction of the migration of the particles towards the cathode or the anode. Zeta-potential can be calculated on the basis of the following formulae:

$$\pm ZP = \frac{v_e}{E} \cdot A$$

and $$A = \frac{4 \cdot \eta}{\epsilon} \cdot 9.10^4$$

wherein $\eta$ stands for the viscosity of the liquid medium, $\epsilon$ represents dielectric permittivity and $9.10^4$ is the conversion factor of the electrostatic unit into Volts.

In case of water, $A = 150$ at a temperature of 20° C. (Martin, A. N. Swarbrick, J. Cammarata, A.: Physical Pharmacy) (Lea and Febiger, Philadelphia 1969, page 458). Determination of ZP on the basis of electrophoretic velocity is carried out in a measuring cell provided with molybdenum or platinum electrodes placed under a special colloidal microscope. The migration speed of the particles can be determined under stable D.C. voltage of known value after a certain time, in a stationary state, by means of a stop-watch, and an ocular micrometer, whereafter the ZP value can be calculated according to the aforementioned formula.

The unavoidable disadvantage of this widely used method is that in the course of electrophoresis, in particular in a medium which also comprises electrolytes, the temperature of the system continuously changes. Thermic flow considerably disturbs electrophoretic migration. In addition, gas evolves on the electrodes, electrochemical processes occur, and in the measuring cell, ions migrate, which causes a deleterious effect on the accuracy of the measurement. The fact that the liquid medium and the particles migrate in the opposite direction along the wall of the cell due to electroendoosmosis makes the measurement especially difficult. Along the vertical wall of the measuring cell the particles migrate with a changing velocity having a parabolic velocity profile. According to said velocity profile, particle velocity reaches its maximum at the axis of the measuring cell, while at the limit of endoosmosis it equals zero. Between this limit and the wall of the measuring cell the particles migrate in the opposite direction.

From the foregoing it is obvious that measuring of ZP on the basis of the electrophoretic migration speed is very difficult. Complicated apparatus is required; in addition, measuring errors frequently exceed 10%.

In the prior art several other ZP measuring methods are known. These include the method based on measuring the electroosmosis formed under the influence of electric field of force (Biefer, G. J., Mason S. G.: Colloid Sci. 9, 20) (1954); or on measuring flow potential (among others Martin, W. McK., Gortner, R. A.: J. Phys. Chem. 34 1509) (1930); or on the basis of measuring volumetric flow or potential of sedimentation. According to specific embodiments of these techniques, the measurement may be carried out in double microcapillary tubes in an electrophoretic cell; or using the phenomena of zone-electrophoresis, the relationship of moving phase borders and mass flow; or by electrophoretic light dispersion, laser technique (Robert J. Hunter: Zeta Potential in Colloid Science (Acad. Press London, 1981), pages 127–175). However, such apparatus is either not commercially available or if available, it is very expensive. Additionally, these methods of determining ZP are laborious and time consuming. Moreover, accuracy of measurement is limited to a variation coefficient of ±5%. In several professional fields, among others in the chemical and pharmaceutical industry, when plant-protecting agents, cosmetics and drugs are produced, or when the filtering processes are optimized in the chemical industry, sewage treatment, and drinking water purification, the accurate determination of the ZP-value of colloids and suspensions is critical.

Stabilization of suspensions and prevention of the aggregation of the suspended particles is possible by regulation of the ZP-value and proper choice of the additives on basis of ZP-measurements. In technical literature it has been generally accepted that suspensions with a ZP-value of −100 nV are extraordinarily stable. In order to increase efficiency of filtering processes (the aggregation of the particles) the ZP-value should be reduced. Proper choice of additives or conditions also requires measuring of the ZP-value.

An object of the invention is to improve the known techniques of measuring of ZP-value in order to develop a process which is easy to conduct, requires less work, and provides accurate measurements.

DESCRIPTION OF THE INVENTION

Figure 1:
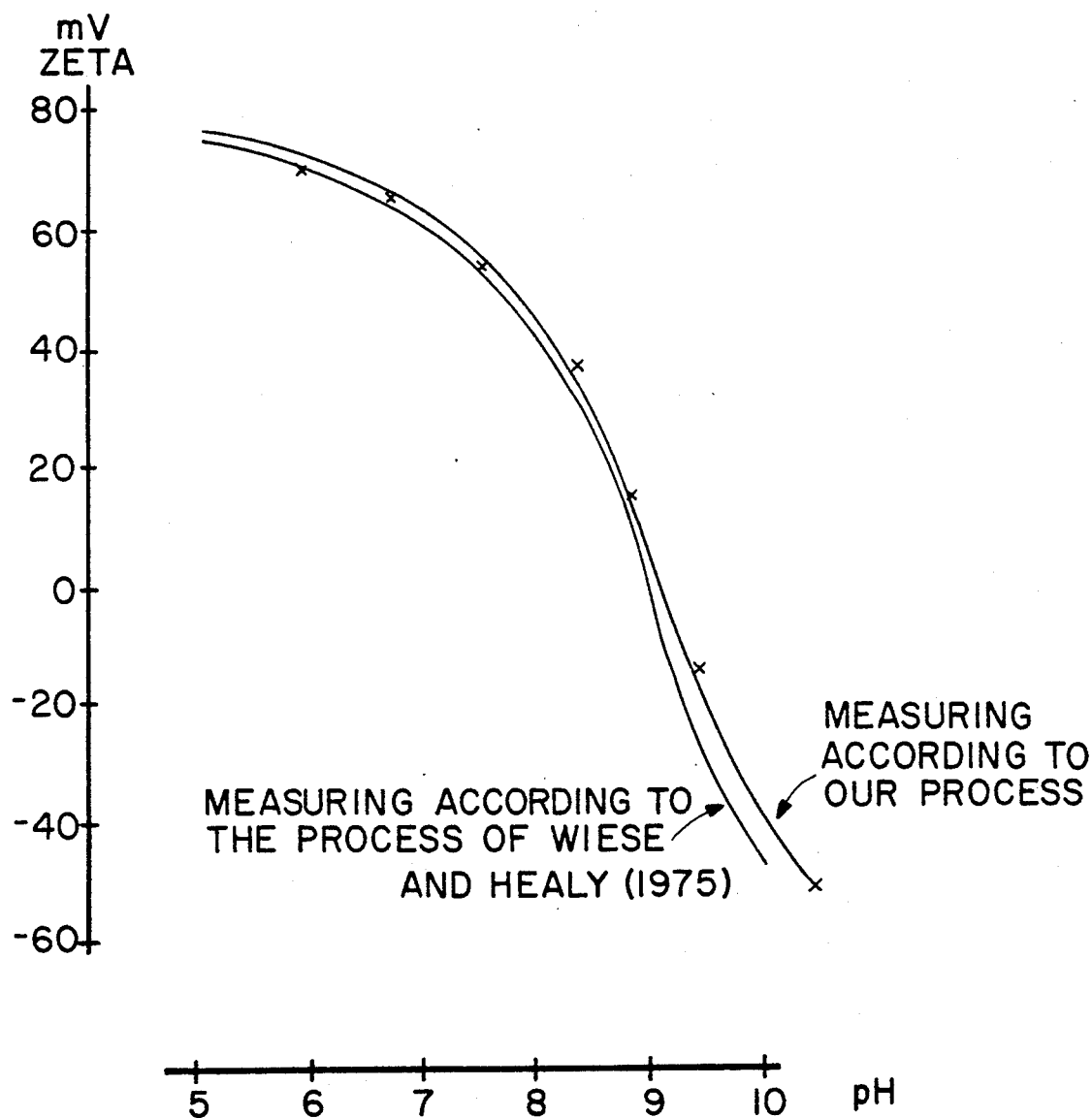
FIG. 1 is a comparative graph of measurements of zeta potential vs. pH according to the prior art and according to the invention.
Figure 2:
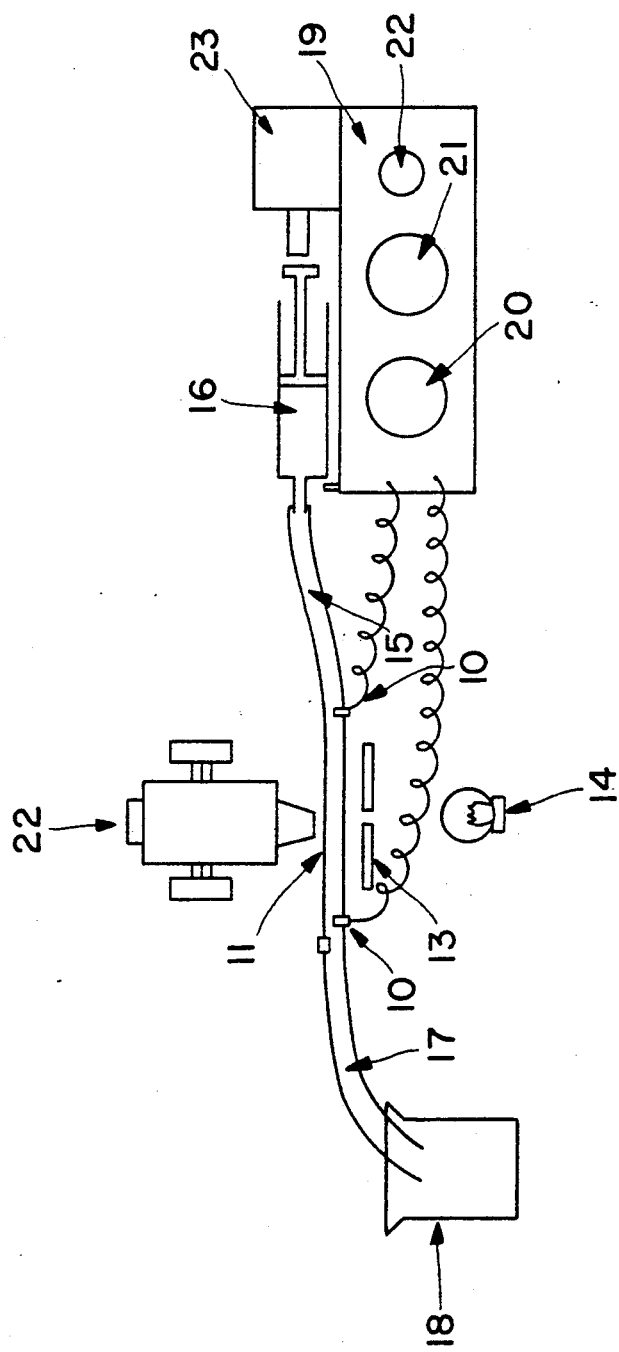
FIG. 2 is a schematic of the apparatus for carrying out the method of the invention.

Surprisingly we have found that the electrophoretic migration of suspended material particles can be produced not only in a D.C. voltage field of force. But by allowing the suspension to flow laminarly and equally in time in an adequate apparatus, and by switching on the proper + or − pole in the direction of flow and applying momentary controlled direct voltage of proper magnitude it may be produced. According to the process of the invention, the $v_e$ electrophoretic migration speed can be calculated in another way than described in the prior art. It is observed that local flow velocity (v) of the selected particle changes to the flow velocity $v_V$ due to the effect of the voltage V applied. In this case the particle does not stop but travels slower or faster depending on the energized direction of poles. In case, the negative pole is switched in the direction of flow and flow velocity of the particle decreases upon the effect of the voltage V, the sign of the ZP-value will be negative; otherwise it is positive. On the basis of the expression $$v \pm v_V = v_e$$

electrophoretic migration speed $v_e$ can be calculated (expressed in units cm.s$^{-1}$) and in such a manner ZP can be given by using the formula as described.

According to a preferred embodiment of the process, in the constantly flowing liquid the particle intended to be observed will stop, as the magnitude of the electrophoretic velocity arising under the effect of the voltage complies with the velocity of liquid flow. ZP-value can be calculated by using the previously described equation, considering that the velocity of flow of the particle corresponds to the value $v_e$.

According to a preferred embodiment of the method of the invention, two 0.2 mm thick platinum electrodes 10 spaced apart 10.0 cm are installed in a cylindrical glasspipe 11 having an inner diameter of 3 to 6 mm, preferably 4 mm. Thereafter the measuring pipe 11 is placed under a microscope 12 suitable for 15-30-fold magnification and provided with a calibrated ocular micrometer scale. The suspension is illuminated by fibre-optics or by means of a 100 micron optical slot 13 arranged before the microscope lamp 14 to eliminate the disturbing (heating) effect of the light source. One end of the measuring pipe is coupled by a synthetic connection 15 to an injector 16 of 2-10 cm$^3$, containing the suspension to be tested, while the other end is coupled by a synthetic connection 17 to a vessel 18 for receiving the suspension flowing through the measuring pipe. When entering the suspension into the system, care is to be taken to avoid air bubbles when filling the measuring pipe 11, the connecting synthetic pipes 15, 17 and the injector 16. Thereafter the injector 16 is fitted into the equipment and the suspension is allowed to flow at a regulated, steady-state velocity. The electrodes 10 (made of platinum) of the measuring pipe are connected to a D.C. voltage supply unit 19 provided with an alternator or pole changer switch 20 and with a stabilized voltmeter 21 which works in the voltage range between 1 and 800 V. Steady flow of the particles in the microscope 22 can be controlled by measuring the travelling time of the selected particle, observing the same through the 100-scale of the ocular micrometer, with an accuracy of 0.01 s, separately in the first and second 50—50 pitch of the scale. If the particle takes the first and second 50 pitch within about the same time (0.01-0.02 s difference is acceptable), the flow in the system is considered to be steady-state, laminar. Thereafter, another particle is selected and the travelling time thereof is measured at an optional distance (10, 20, . . . 50 ocular pitch) with an accuracy of 0.01 s. Then the D.C. voltage 19 is switched on, the pole changer 20 is positioned, and by regulating voltage controller 22 the voltage applied to the measuring pipe 11 the motion of the chosen particle should stop. This voltage value is registered. The flow velocity measured with the calibrated ocular micrometer with an accuracy of 0.01 s is calculated to $V_e$=cm.s$^{-1}$ units with an accuracy of four digits. Dividing the voltage needed for stopping the particle by the distance of the electrodes (in the present case, ten cm.), the value E of voltage density is obtained. In this manner using the known formula $$ZP = \frac{V_e}{E} \cdot 150$$

the ZP-value of the desired aqueous suspension can be calculated.

It is recommended to perform measurements of a large series of particles migrating with different speeds. Thus, the average of the ZP-values and a variation coefficient or standard deviation can be calculated by using known mathematic statistical methods. These values characterize the accuracy of measuring.

The testing method may be varied, e.g. by scanning the flowing particles, a ZP-value of the selected particle can be determined by simultaneously regulating flow velocity and the voltage applied to the measuring pipe.

According to a preferred embodiment of the measuring system apparatus suitable for carrying out the method of the invention, includes a measuring pipe 11 with an inner diameter—within the range 3 to 6 mm—, into which platinum electrodes 10 (dia. 0.2 mm) at a spacing of 10.0 cm are installed. The measuring pipe is fixed with the usual clamping plates to the stage of the microscope 22. Illumination is provided by fibre-optics instead of a condenser or with a 100 micron optical slot 13 arranged in front of the condenser. The ocular micrometer is calibrated and the path length of the particles is calculated in cm. For quickly sedimenting suspensions, it is advantageous to position the microscope at an angle of 90° with the stage of the microscope turned from the horizontal to vertical. In this case, the sedimenting particle bends from the line of the ocular micrometer scale, making it possible to examine only those particles which are travelling parallel with the axis of the measuring pipe and with the scale line of the ocular micrometer.

The sample to be tested is fed by a syringe 16 (injector). Practically, for low velocities an injector with a smaller volume is used; if higher velocities are needed, injectors with a larger volume should be used. For this purpose the so-called tuberculine injectors with a volume of 2, 5, perhaps 10 cm$^3$ may be used. Injectors with a far larger volume are recommended only in the case of extremely high ZP-values.

The connecting pipes 15, 17 are made of polyethylene or any other structural material. The sample feeder 23 is advantageously the Hungarian "INFUCONT" quartz-controlled electronic apparatus, which is well suited for the control of the "INFUMAT or INFUDRIVER" drives which drive the piston of injector. The electric energy at the proper frequency, phase, and voltage, required for operating the shifting-motor drive at a continuously controllable rate of feeding is electronically digitally displayed. The digital display (D) includes the feeder and flow velocity observed in the measuring pipe (with an inner diameter of 5.0 mm (expressed in cm.s$^{-1}$) controlled with a 10 cm$^3$ synthetic syringe). Within the digital display range 0-40, the apparatus delivered the aqueous suspension with an acceptable linearity. In the described arrangement the linear regression coefficient $$(cm.s^{-1}) = 0.00141. D$$

was found to be 0.9999. The solution of the linear equation will yield values, when using measuring pipes or injectors with different inner diameters. Thus calibration is required for individual arrangements of given dimensions.

It is well known that a pure laminar flow will be established in a cylindrical pipe within the range of contemplated velocity, based on the low Reynolds-number. The velocity distribution curve has a parabolic shape. Along the axis of the pipe, the flow velocity is double the average flow velocity ($\bar{v}$). The optimal radius r of the cross-section of the radius $r_o$ the local flow velocity v can be calculated on basis of the Knudsen and Katz rule $$\frac{v}{\bar{v}} = 2 \left(1 - \frac{r^2}{r_o^2}\right)$$

(John H. Perry: Manual of Chemical Engineers, Technical Publishers, Budapest, 1953. Volume I, page 564). From this it becomes obvious that in the microscope, in dependence of the depth of focus, at a relatively high velocity (above 100 micron.s$^{-1}$), parabolic velocity distribution becomes flattened to such an extent that in its visual field particles travelling with different speeds can be observed. At considerably lower velocities particles travelling with nearly identical velocities can be observed.

According to an improved mode of realization of the process according to the invention, the measuring pipe 11 is placed on the microscope 12—as detailed previously—, the injector 16 is arranged in the feeding device 23 and connection is made with synthetic pipes 15, 17. The feeder 23 is calibrated for the suspension to be examined, as specified earlier. The flow velocity of the particles is twice the digital signal of the feeder. By the aid of the voltage regulator of the D.C. voltage current source 19, the voltage needed for stopping the particles is adjusted. Care should be taken that the pole switch 20 is in the proper direction, in compliance with the nature of the material tested.

The feeder 23 and the D.C. voltage supply unit 19 deliver an electric signal proportional with the flow velocity and the voltage value needed for stopping the particles, these two signals are fed to a computer and display unit. Thereafter, based on a predetermined algorithm, the ZP-value of the material tested is obtained automatically.

Accuracy of the measuring system and the testing method are illustrated by the following examples

Example 1

2–3 mg of 17α-hydroxy-21-acetoxy-corticosterone, as a basic material with a grain size below 10 microns, are mixed with a small quantity of water in a frictional mortar. The mixture thus obtained is diluted with 50 cm$^3$ of distilled water and allowed to stand for three days. Measurement is obtained with a measuring pipe having an internal diameter of 4.0 nm with electrodes arranged therein with a spacing of 10 cm; a 5 cm$^3$ synthetic injector; and a microscope with 10 X magnification. The flow time on the 1000 micron path in second(s), as well as voltage required for stopping the particle are determined.

Thereafter further measuring is performed for a 318 microns path with 30 X magnification. ZP-values calculated from the measured data are as follows:

| s | V | ZP |
|---|---|---|
| *1000 microns path* | | |
| 11.0 | 230 | −59.3 |
| 12.0 | 222 | −56.3 |
| 12.0 | 222 | −56.3 |
| *318 microns path* | | |
| 3.80 | 220 | −57.1 |
| 3.73 | 220 | −58.1 |
| 3.73 | 219 | −58.4 |
| 3.93 | 205 | −59.2 |
| 3.87 | 208 | −59.3 |

Average value: −58.0 coefficient of variation ±1.2 (±2.07%).

These test results demonstrate well that the measuring system and the testing method of the invention can be used for determining the ZP-value with an accuracy which corresponds to and often exceeds the experiences reported heretofore in technical literature.

In technical literature ZP-value has been referred to generally as an "apparent" value, form which conclusions can be drawn on the inaccuracies resulting from the difficulties of determination. Taking into consideration that measuring technique based on a flow system eliminates numerous disturbing factors, a ZP-value determined in that way may be considered as a virtual value. In order to be able to demonstrate reproducibility of the data of technical literature, comparative tests were also carried out.

Example 2 (comparative example)

In the earlier described manner, colloidal iron(III)hydroxide was tested in freshly boiled and cooled distilled water at 22° C. after having precipitated ferric-chloride with sodium hydroxide and eliminated chlorine. Measured results:

| | 318 microns path: | |
|---|---|---|
| s | V | ZP mV |
| 4.58 | 235 | −44.3 |
| 4.80 | 220 | −45.1 |
| 4.76 | 222 | −45.1 |
| 4.90 | 215 | −45.3 |
| 5.00 | 231 | −41.3 |
| 5.57 | 203 | −42.2 |
| 6.43 | 181 | −41.0 |
| 7.12 | 162 | −41.3 |

Average ZP value: −43.23 mV
Variation coefficient: ±1.78 (±4.11%)
The value given in the technical literature is 45 mV; the difference is −3.93% (Martin, A. N. et al. Physical Pharmacy (Lea and Febiger, Philadelphia 1969) page 458).

ZP-value is considerably influenced by traces of carbonic acid impurities in water, or chloride ion impurities of the sample; the comparison to the value of technical literature is considered good.

Example 3 (Comparative Example)

The second coparative test performed for determining ZP-values in alumina/$10^{-4}$M potassium-nitrate solution in dependence of pH was carried out as previously described (Wiese, R. G. et al.: Colloid Interface Sci. 51, 427) (1975)); the results obtained are reflected in FIG. 1.

FIG. 1 illustrates that the ZP-values measured in the flowing system show a good comparison with the data of technical literature. Difference of larger extent, as observed in high pH-ranges may result from the differences in the structure of the solid material tested in addition to the error sources as mentioned before.

Example 4

Comparative test for comparing the ZP-values of polymorphous crystal modifications It is well known that some elements have allotropic structure. Organic compounds can be produce in several crystal modifications, e.g. the pesticidal pharmaceutical basic material Mebendazol, the three polymorphous crystal modifications (A, B and C) of which are known (Láncos; Krisztina: Ph.D. thesis, Medical University Semmelweis, Pharmaceutical Institute, Budapest, 1985). In respect to chemical composition, the single Mebendazol polymorphes are quite identical, however, the structure of their solid body is reversibly different. Three Mebendazol polymorphous crystal modifications we comminuted to a grain size finer than 30 microns and 2 mg thereof were suspended in distilled water. ZP-value was measured in a flowing system at 20° C. temperature, as specified earlier. The average value of six measurements and variation coefficient of the measuring series were, as follows:

| sample | $ZP_{mV}$ | ± |
|---|---|---|
| Mebendazol A | 106.3 | 2.1 |
| Mebendazol B | 34.9 | 0.9 |
| Mebendazol C | 104.0 | 3.0 |

Example 5

Stabilization of the suspension by controlling the ZP-value by using additives

According to technical literature stability of a suspension is considered as maximally satisfactory, if the value of ZP is approximately −100 mV. The stability of the suspension does not meet the requirements if the ZP-value thereof is lower; under −40 agglomeration and under −10 precipitation will occur.

By means of auxiliary materials absorbed onto the surface of the solid body, properties of the so-called electric double-layer and thus the ZP-value can be controlled. The possibility of ZP-value regulation is illustrated by the example of the aqueous suspension of 17α-hydroxy-21-acetoxycorticosterone, as specified hereinabove.

If ZP-value is measured in distilled water, at a temperature of 20° C. in the presence of different auxiliary materials, as described earlier, the following results are obtained:

| mg · cm$^{-3}$ auxiliary materials | ZP mV | ± |
|---|---|---|
| ∅ (in pure distilled water) | −58.0 | 1.2 |
| 0.5 sodium stearate | −74.0 | 2.0 |
| 0.5 Tween-80 | −81.0 | 1.4 |
| 0.5 + 0.5 sodium stearate + Tween-80 | −140.2 | 4.1 |

We claim:
1. A method for determining the zeta-potential of a material suspended in a liquid medium which comprises,
   (a) streaming the suspension in a laminar flow,
   (b) subjecting the laminarly flowing suspension to the effect of selectively applied and controlled D.C. voltage,
   (c) selecting a particle for optical examination and determining the electrophoretic velocity from induced changes of flow velocity in the selected particle as a function of the applied voltage, and
   (d) utilizing said determination to calculate the zeta-potential.
2. The method of claim 1, in which,
   (a) the laminarly flowing suspension is subjected to said controlled D.C. voltage until the motion of said selected particle stops,
   (b) measuring the applied voltage and obtaining the flow velocity of the particle as electrophoretic velocity, and
   (c) thereafter using said determination to calculate the zeta-potential.
3. Apparatus for use in determining the zeta-potential of particles of a material suspended in a liquid medium comprising;
   (a) an injector means for containing and delivering by laminar flow a sample of the material to be tested;
   (b) a transparent measuring pipe for receiving at one end said sample from said injector means;
   (c) vessel means for receiving said laminarly flowing sample from the other end of said transparent pipe;
   (d) connecting pipe means linking said infector means and said injector means and said vessel means to said measuring pipe;
   (e) spaced electrodes supported in said measuring pipe;
   (f) microscope means having an ocular micrometer adjacent to said measuring pipe of sufficient optical power to observe suspended particles;
   (g) voltage supply means for energizing said electrodes with D.C. voltage;
   (h) voltage control means for adjusting and measuring the D.C. voltage applied to said electrodes for stopping the motion of an observed particle.

* * * * *